US006844131B2

(12) United States Patent
Oberlander et al.

(10) Patent No.: US 6,844,131 B2
(45) Date of Patent: Jan. 18, 2005

(54) POSITIVE-WORKING PHOTOIMAGEABLE BOTTOM ANTIREFLECTIVE COATING

(75) Inventors: Joseph E. Oberlander, Phillipsburg, NJ (US); Ralph R. Dammel, Flemington, NJ (US); Shuji Ding-Lee, Branchburg, NJ (US); Mark O. Neisser, Whitehouse Station, NJ (US); Medhat A. Toukhy, Flemington, NJ (US)

(73) Assignee: Clariant Finance (BVI) Limited, Tortola (VG)

( * ) Notice: Subject to any disclaimer, the term of this patent is extended or adjusted under 35 U.S.C. 154(b) by 83 days.

(21) Appl. No.: 10/042,532

(22) Filed: Jan. 9, 2002

(65) Prior Publication Data

US 2003/0129531 A1 Jul. 10, 2003

(51) Int. Cl.[7] .................................. G03F 7/004
(52) U.S. Cl. ................... 430/270.1; 430/271.1; 430/905
(58) Field of Search .................. 430/271.1, 270.1, 430/905, 326

(56) References Cited

U.S. PATENT DOCUMENTS

| | | |
|---|---|---|
| 4,491,628 A | 1/1985 | Ito et al. |
| 4,521,274 A | 6/1985 | Reichmanis et al. |
| 4,557,797 A | 12/1985 | Fuller et al. |
| 4,557,996 A | 12/1985 | Aoyama et al. |
| 4,863,827 A | 9/1989 | Jain et al. |
| 4,910,122 A | 3/1990 | Arnold et al. |
| 5,069,997 A | 12/1991 | Schwaim et al. |
| 5,350,660 A | 9/1994 | Urano et al. |
| 5,354,643 A | 10/1994 | Cabrera et al. |
| 5,581,730 A | 12/1996 | Silla |
| 5,585,219 A | 12/1996 | Kaimoto et al. |
| 5,635,333 A | 6/1997 | Peterson et al. |
| 5,652,297 A | 7/1997 | McCulloch et al. |
| 5,693,691 A | 12/1997 | Flaim et al. |
| 5,695,910 A | 12/1997 | Urano et al. |
| 5,716,756 A | 2/1998 | Pawlowski et al. |
| 5,731,386 A | 3/1998 | Thackeray et al. |
| 5,763,135 A | 6/1998 | Ding et al. |
| 5,880,169 A | 3/1999 | Osawa et al. |
| 5,882,996 A | 3/1999 | Dal |
| 5,886,102 A | 3/1999 | Sinta et al. |
| 5,935,760 A | 8/1999 | Shao et al. |
| 5,939,236 A | 8/1999 | Pavelcheck et al. |
| 5,981,145 A | 11/1999 | Ding et al. |
| 6,042,990 A | 3/2000 | Shao et al. |
| 6,054,254 A | 4/2000 | Sato et al. |
| 6,080,530 A | 6/2000 | Shao et al. |
| 6,110,641 A | 8/2000 | Trefonas, III et al. |
| 6,110,653 A | 8/2000 | Holmes et al. |
| 6,114,085 A | 9/2000 | Padmanaban et al. |
| 6,187,506 B1 | 2/2001 | Ding et al. |
| 6,242,161 B1 | 6/2001 | Kawaguchi et al. |
| 6,251,562 B1 | 6/2001 | Breyta et al. |
| 6,261,743 B1 | 7/2001 | Pavelchek et al. |
| 6,319,651 B1 | 11/2001 | Holmes et al. |
| 2003/0104322 A1 * | 6/2003 | Yamashita et al. |

FOREIGN PATENT DOCUMENTS

| | | |
|---|---|---|
| DE | 3930086 | 3/1991 |
| DE | 3930087 | 3/1991 |
| DE | 41 12 967 A1 | 10/1992 |
| DE | 4112967 | 10/1992 |
| EP | 542008 | 10/1992 |
| EP | 0 542 008 A1 | 5/1993 |
| EP | 583205 | 6/1993 |
| EP | 0 726 500 A1 | 8/1996 |
| EP | 0 794458 | 3/1997 |
| EP | 0 813 114 | 5/1997 |
| EP | WO 97/33198 | 9/1997 |
| EP | 0 813 114 A2 | 12/1997 |
| EP | 0 905 565 A1 | 3/1999 |
| EP | 2357 509 A | 6/2001 |
| GB | 2135 793 | 9/1984 |
| GB | 2320718 | 7/1998 |
| JP | 10 301268 A | 11/1998 |
| JP | 2000 171604 A | 6/2000 |

OTHER PUBLICATIONS

K. Bather et al, "TiN, O, As a Barrier Between Cr–Si–(O) and Aluminum Thin Films", Thin Solid Films, 200 (1991) p. 93–117.

C. Nolscher et al, "High contract single layer resists and antireflection layers—an alternative to multilayer resist techniques", SPIE vol. 1086 Advances in Resist Technology and Processing VI (1989) p. 242–250.

G. Czech et al, "Reduction of Lindwidth Variation for the Gate Conductor Level by Lithography Based on a New Antireflective Layer", Microelectronic Engineering 21 (1993) pp. 51–56.

(List continued on next page.)

Primary Examiner—Rosemary Ashton
(74) Attorney, Agent, or Firm—Sangya Jain

(57) ABSTRACT

The present invention relates to a novel absorbing, photoimageable and aqueous developable positive-working antireflective coating composition comprising a photoacid generator and a polymer comprising at least one unit with an acid labile group and at least one unit with an absorbing chromophore. The invention further relates to a process for using such a composition. The present invention also relates to a novel absorbing, photoimageable and aqueous alkali developable positive-working antireflective coating composition comprising a polymer comprising at least one unit with an acid labile group, a dye and a photoacid generator. The invention further relates to a process for using such a composition. The invention also relates to a novel process for forming a positive image with a positive photoresist and a novel photoimageable and aqueous developable positive-working antireflective coating composition, where the antireflective coating comprises a polymer comprising an acid labile group. The invention further relates to such a composition. The invention also relates to a process for imaging a photoimageable antireflective coating composition.

23 Claims, No Drawings

OTHER PUBLICATIONS

F. M. Houlihan et al, "Chemically Amplified Resists: The Chemistry and Lithographic Characteristics of Nitrobenzyl Benzenesulfonate Derivatives", Journal of Photopolymer Science and Technology, vol. 3, No. 3 (1990) pp. 259–273.

T. Yamaoka et al, "Photochemical Dissociation of p–Nitrobenzyl Aromatic Sulfonate and Its Application to Chemical Amplification Resists", Journal of Photopolymer Science and Technology, vol. 3, No. 3 (1990) pp. 275–280.

Masamitsu Shirai et al, "Photochemistry of Imino Sulfonate Compounds and Their Application to Chemically Amplified Resists", Journal of Photopolymer Science and Technology, vol. 3, No. 3 (1990) pp. 301–304.

Leo Schlegel et al, "Studies on the Acid Formation and Deprotection Reaction by Novel Sulfonates in a Chemical Amplification Positive Photoresist", Journal of Photopolymer Science and Technology, vol. 3, No. 3 (1990) pp. 281–287.

James Fahey et al, "Design of a Bottom Anti–Reflective Layer for Optical Lithography", SPIE, vol. 2195, pp. 422–2195.

* cited by examiner

POSITIVE-WORKING PHOTOIMAGEABLE BOTTOM ANTIREFLECTIVE COATING

FIELD OF INVENTION

The present invention relates to novel positive-working, photoimageable, and aqueous developable antireflective coating compositions and their use in image processing by forming a thin layer of the novel antireflective coating composition between a reflective substrate and a photoresist coating. Such compositions are particularly useful in the fabrication of semiconductor devices by photolithographic techniques, especially those requiring exposure with deep ultraviolet radiation.

BACKGROUND

Photoresist compositions are used in microlithography processes for making miniaturized electronic components such as in the fabrication of computer chips and integrated circuits. Generally, in these processes, a thin coating of a film of a photoresist composition is first applied to a substrate material, such as silicon wafers used for making integrated circuits. The coated substrate is then baked to evaporate any solvent in the photoresist composition and to fix the coating onto the substrate. The baked and coated surface of the substrate is next subjected to an image-wise exposure to radiation.

This radiation exposure causes a chemical transformation in the exposed areas of the coated surface. Visible light, ultraviolet (UV) light, electron beam and X-ray radiant energy are radiation types commonly used today in microlithographic processes. After this image-wise exposure, the coated substrate is treated with a developer solution to dissolve and remove either the radiation-exposed or the unexposed areas of the photoresist.

There are two types of photoresist compositions, negative-working and positive-working. When positive-working photoresist compositions are exposed image-wise to radiation, the areas of the photoresist composition exposed to the radiation become soluble in a developer solution (e.g. a rearrangement reaction occurs) while the unexposed areas of the photoresist coating remain relatively insoluble to such a solution. Thus, treatment of an exposed positive-working photoresist with a developer causes removal of the exposed areas of the photoresist coating and the formation of a positive image in the coating, thereby uncovering a desired portion of the underlying substrate surface on which the photoresist composition was deposited. In a negative-working photoresist the developer removes the portions that are not exposed.

The trend towards the miniaturization of semiconductor devices has led both to the use of new photoresists that are sensitive to lower and lower wavelengths of radiation, and also to the use of sophisticated multilevel systems to overcome difficulties associated with such miniaturization.

High resolution, chemically amplified, deep ultraviolet (100–300 nm) positive and negative tone photoresists are available for patterning images with less than quarter micron geometries. There are two major deep ultraviolet (uv) exposure technologies that have provided significant advancement in miniaturization, and these are lasers that emit radiation at 248 nm and 193 nm. Examples of such photoresists are given in the following patents and incorporated herein by reference, U.S. Pat. Nos. 4,491,628, 5,350,660, EP 794458 and GB 2320718. Photoresists for 248 nm have typically been based on substituted polyhydroxystyrene and its copolymers. On the other hand, photoresists for 193 nm exposure require non-aromatic polymers, since aromatics are opaque at this wavelength. Generally, alicyclic hydrocarbons are incorporated into the polymer to replace the etch resistance lost by eliminating the aromatic functionality. Furthermore, at lower wavelengths the reflection from the substrate becomes increasingly detrimental to the lithographic performance of the photoresist. Therefore, at these wavelengths antireflective coatings become critical.

The use of highly absorbing antireflective coatings in photolithography is a simpler approach to diminish the problems that result from back reflection of light from highly reflective substrates. Two major disadvantages of back reflectivity are thin film interference effects and reflective notching. Thin film interference, or standing waves, result in changes in critical line width dimensions caused by variations in the total light intensity in the resist film as the thickness of the resist changes. Reflective notching becomes severe as the photoresist is patterned over substrates containing topographical features, which scatter light through the photoresist film, leading to line width variations, and in the extreme case, forming regions with complete photoresist loss.

The use of bottom antireflective coatings provide the best solution for the elimination of reflectivity. The bottom antireflective coating is applied on the substrate and then a layer of photoresist is applied on top of the antireflective coating. The photoresist is exposed imagewise and developed. The antireflective coating in the exposed area is then typically etched and the photoresist pattern is thus transferred to the substrate. Most antireflective coatings known in the prior art are designed to be dry etched. The etch rate of the antireflective film needs to be relatively high in comparison to the photoresist so that the antireflective film is etched without excessive loss of the resist film during the etch process. There are two known types of antireflective coatings, inorganic coatings and organic coatings. However, both of these types of coatings have so far been designed for removal by dry etching.

Inorganic type of coatings include such films as TiN, TiON, TiW and spin-on organic polymer in the range of 30 nm, and are discussed in the following papers: C. Nolscher et al., Proc SPIE vol. 1086, p242 (1989); K. Bather, H. Schreiber, Thin solid films, 200, 93, (1991); G. Czech et al., Microelectronic Engineering, 21, p.51 (1993). Inorganic bottom antireflective coatings require precise control of the film thickness, uniformity of film, special deposition equipment, complex adhesion promotion techniques prior to resist coating, separate dry etching pattern transfer step, and dry etching for removal. Another very important aspect of dry etching is that the harsh etch conditions can cause damage to the substrate.

Organic bottom antireflective coatings are more preferred and have been formulated by adding dyes to a polymer coating solution or by incorporating the dye chromophore into the polymer structure, but these too need to be dry etched down to the substrate. Polymeric organic antireflective coatings are known in the art as described in EP 583,205, and incorporated herein by reference. It is believed that such antireflective polymers are very aromatic in nature and thus have too low a dry etch rate, especially relative to the new type of non-aromatic photoresists used for 193 nm and 157 nm. In addition, photoresist patterns may be damaged or may not be transferred exactly to the substrate if the dry etch rate of the antireflective coating is similar to or less than the etch rate of the photoresist coated on top of the antireflective coating. The etching conditions for removing the organic coatings can also damage the substrate. Thus, there is a need for organic bottom antireflective coatings that do not need to be dry etched especially for compound semiconductor type substrates, which are sensitive to etch damage.

The novel approach of the present application is to use an absorbing, photoimageable positive working bottom antireflective coating that can be developed by an aqueous alkaline solution, rather than be removed by dry etching. Aqueous removal of the bottom antireflective coating eliminates the dry etch rate requirement of the coating, reduces the cost intensive dry etching processing steps and also prevents damage to the substrate caused by dry etching. The absorbing bottom anfireflective coating compositions of the present invention contain a photoactive compound and a polymer, which on exposure to light of the same wavelength as that used to expose the top positive photoresist become imageable in the same developer as that used to develop the photoresist. This process greatly simplifies the lithographic process by eliminating a large number of processing steps. Since the antireflective coating is photosensitive, the extent of removal of the antireflective coating is defined by the latent optical image, which allows a good delineation of the remaining photoresist image in the antireflective coating.

The antireflective composition disclosed in EP 542 008, is based on highly aromatic polymers, such as novolaks, polyvinyl phenols, copolymers of polyvinyl phenol and styrene or alphamethyl styrene, etc. Furthermore, this antireflective coating is not photoimageable and must be dry etched. Planarizing coatings that can optionally contain absorbing components are known and have been used to planarize topographical features and also prevent reflections. Planarizing layers are fairly thick and are of the order of 1 or 2 microns. Such layers are described in GB 2135793, U.S. Pat. Nos. 4,557,797 and 4,521,274. However these layers must be either dry etched or removed with an organic solvent, such as methyl isobutyl ketone. In the semiconductor industry removal of coatings by aqueous solutions is greatly preferred over organic solvents.

Bilevel photoresists are known, as in U.S. Pat. No. 4,863,827, but require exposure of two different wavelengths for the top and bottom photoresists, which complicates the processing of the lithography.

There are many patents that disclose antireflective coating compositions but these coatings are all cured to be insoluble in an aqueous developer solution and must be removed by dry etching. U.S. Pat. No. 5,939,236 describes an antireflective coating containing a polymer, an acid or thermal acid generator, and a photoacid generator. However this film is completely crosslinked to make it insoluble in an alkaline aqueous developer solution. The film is removed by a plasma gas etch. Examples of other antireflective coating patents are U.S. Pat. Nos. 5,886,102, 6,080,530 and 6,251,562.

U.S. Pat. No. 4,910,122 discloses an aqueous developable antireflective coating, however the degree of solubility of the total film is controlled by the bake conditions. This antireflective coating is not photoimageable, and therefore, there are no clearly defined soluble and insoluble regions in the film. The dissolution of the antireflective coating is controlled by bake conditions and thus the antireflective coating is very sensitive to the developer normality and developing time, and also gives poor resolution. High normality developer and/or long develop times can cause excessive removal of the antireflective coating.

Another process for imaging photoresists using antireflective coatings is disclosed in U.S. Pat. No. 5,635,333, however, the antireflective coating is not developed at the same time as the photoresist.

U.S. Pat. No. 5,882,996 describes a method of patterning dual damascene interconnections where a developer soluble antireflective coating interstitial layer is used. The antireflective coating is formed between two photoresist layers and has a preferred thickness of 300–700 angstroms, refractive index of 1.4–2.0 and is water soluble. The antireflective coating is not photoimageable and there is no description of the chemistry of the antireflective coating.

An acid sensitive antireflective coating is disclosed in U.S. Pat. No. 6,110,653, where the antireflective coating is crosslinked by a heating step and is subsequently rendered water soluble in the presence of an acid. The antireflective coating described contains a water soluble resin and a crosslinker, but other components, such as dyes, photoacid generators or amine base may be added. In this invention the water soluble resin is crosslinked before exposure, and if the composition additionally contains a photoacid generator, then the resin is uncrosslinked prior to development.

The novel antireflective composition of the present invention relates to a photoimageable, aqueous alkali developable, positive-working antireflective coating that is imaged with the same wavelength of light as is used to expose the positive photoresist, and thus is imagewise exposed in a single processing step. It is further heated, and then developed using the same developer and at the same time as the photoresist. The combination of single exposure step and single development step greatly simplifies the lithographic process. Furthermore, an aqueous developable antireflective coating is highly desirable for imaging with photoresists that do not contain aromatic functionalities, such as those used for 193 nm and 157 nm exposure. The novel composition enables a good image transfer from the photoresist to the substrate, and also has good absorption characteristics to prevent reflective notching and line width variations or standing waves in the photoresist. Furthermore, the novel antireflective coating can be designed, by using the appropriate photosensitivity, to function as an antireflective coating at any imaging wavelength. Additionally, substantially no intermixing is present between the antireflective coating and the photoresist film. The antireflective coatings also have good solution stability and form thin films with good coating quality, the latter being particularly advantageous for lithography. When the antireflective coating is used with a photoresist in the imaging process, clean images are obtained, without damaging the substrate.

SUMMARY OF THE INVENTION

The present invention relates to a positive bottom photoimageable antireflective coating composition which is capable of being developed in an aqueous alkaline developer and which is coated below a positive photoresist, where the antireflective coating composition comprises a photoacid generator and a polymer comprising at least one unit with an acid labile group and at least one unit with an absorbing chromophore. The invention further relates to a process for using such a composition for forming an image.

The invention also relates to a positive bottom photoimageable antireflective coating composition which is capable of being developed in an aqueous alkaline developer and which is coated below a positive photoresist, where the antireflective coating composition comprises a photoacid generator, a dye and a polymer comprising at least one unit with an acid labile group. The invention further relates to a process for using such a composition for forming an image.

The invention also relates to a positive bottom photoimageable antireflective coating composition which is capable of being developed in an aqueous alkaline developer and which is coated below a positive photoresist, where the antireflective coating composition comprises a polymer comprising at least one unit with an acid labile group. The invention further relates to a process for using such a composition for forming an image.

The invention also relates to a process for forming a positive image comprising;
a) providing a coating of the bottom photoimageable and alkali developable antireflective coating composition on a substrate;
b) providing a coating of a top photoresist layer;
c) imagewise exposing the top and bottom layer to actinic radiation of same wavelength;
d) postexposure baking the substrate; and,
e) developing the top and bottom layer with an aqueous alkaline solution.

DESCRIPTION OF THE INVENTION

The present invention relates to a novel absorbing, photoimageable and aqueous developable positive-working antireflective coating composition comprising a photoacid generator and a polymer comprising at least one unit with an acid labile group and at least one unit with an absorbing chromophore. The invention further relates to a process for using such a composition. The present invention also relates to a novel absorbing, photoimageable and aqueous alkali developable positive-working antireflective coating composition comprising a polymer comprising at least one unit with an acid labile group, a dye and a photoacid generator. The invention further relates to a process for using such a composition. The invention also relates to a novel photoimageable and aqueous developable positive-working antireflective coating composition, comprising a polymer comprising an acid labile group. The invention further relates to a process for using such composition. The invention also relates to a process for imaging a photoimageable antireflective coating composition.

The antireflective coating composition of the invention is coated on a substrate and below a positive photoresist, in order to prevent reflections in the photoresist from the substrate. This antireflective coating is photoimageable with the same wavelength of light as the top photoresist, and is also developable with the same aqueous alkaline developing solution as that used to typically develop the photoresist. The antireflective coating composition comprises a polymer and a photoacid generator, and is coated on a reflective substrate and baked to remove the solvent of the coating solution. In order to prevent, or minimize, the extent of intermixing between the layers, the components of the antireflective coating are such that they are substantially insoluble in the solvent of the photoresist that is coated on top of the antireflective coating. A positive photoresist is then coated on top of the antireflective coating and baked to remove the photoresist solvent. The coating thickness of the photoresist is generally greater than the underlying antireflective coating. Prior to exposure both the photoresist and the antireflective coating are insoluble in the aqueous alkaline developing solution of the photoresist. The bilevel system is then imagewise exposed to radiation in one single step, where an acid is then generated in both the top photoresist and the bottom antireflective coating. In a subsequent baking step the photogenerated acid reacts with the acid labile group of the polymer in the antireflective coating thus making the polymer soluble in the aqueous alkali developing solution. A subsequent developing step then dissolves the exposed regions of both the positive photoresist and the antireflective coating, leaving the substrate clear for further processing.

The novel antireflective coating that is useful for the novel process of this invention comprises a photoacid generator and a polymer. In the first embodiment of the invention the antireflective coating comprises a photoacid generator and a polymer comprising at least one unit with an acid labile group and at least one unit with an absorbing chromophore. In the second embodiment of the invention the antireflective coating comprises a photoacid generator, a dye and a polymer comprising at least one unit with an acid labile group. Thus the absorbing chromophore may be present within the polymer or as a dye additive in the composition. In a third embodiment the antireflective coating composition comprises a polymer with at least one acid labile group and the absorbing chromophore is either incorporated into the polymer or added as a dye. The antireflective coating does not contain a photoacid generator. In this case the acid from the photoresist diffuses into the antireflective coating during the post exposure bake step, and further deprotects the polymer, making it alkali soluble.

The photoacid generator in the antireflective coating and the photoacid generator in the photoresist are sensitive to the same wavelength of light, thus the same exposure wavelength of light can cause an acid to be formed in both layers. The photoacid generator of the antireflective coating chosen depends on the photoresist to be used. As an example, for a photoresist that is developed for 193 nm exposure, the photoacid generator of the antireflective coating absorbs at 193 nm; and examples of such photoacid generators are onium salts and sulfonate esters of hyroxyimides, specifically diphenyl iodonium salts, triphenyl sulfonium salts, dialkyl iodonium salts and trialkylsulfonium salts. Photoacid generators for antireflective coatings that are designed for use with photoresists for 248 nm exposure can be onium salts, such as diphenyl iodonium salts, triphenyl sulfonium salts and sulfonate esters of hydroxyimides. For exposure at 365 nm the photoacid generator can be diazonaphthoquinones, especially 2,1,4-diazonaphthoquinones that are capable of producing strong acids that can react with the acid labile groups of the polymer. Oxime sulfonates, substituted or unsubstituted naphthalimidyl triflates or sulfonates are also known as photoacid generators. Any photoacid generator that absorbs light at the same wavelength as the top photoresist may be used. Photoacid generators known in the art may be used, such as those disclosed in the U.S. Pat. Nos. 5,731,386, 5,880,169, 5,939,236, 5,354,643, 5,716,756, DE 3,930,086, DE 3,930,087, German Patent Application P 4,112,967.9, F. M. Houlihan et al., J. Photopolym. Sci. Techn., 3:259 (1990); T. Yamaoka et al., J. Photopolym. Sci. Techn., 3:275 (1990)), L. Schlegel et al., J. Photopolym. Sci. Techn., 3:281 (1990) or M. Shirai et al., J. Photopolym. Sci. Techn., 3:301 (1990), and incorporated herein by reference. The acid generated in the exposed regions of the antireflective coating reacts with the polymer containing the acid labile group to make it soluble in the developer, and hence produce a positive image on the substrate without a dry etching step.

The polymer of the novel invention comprises at least one unit with an acid labile group. One function of the polymer is to provide a good coating quality and another is to enable the antireflective coating to change solubility from exposure to development. The acid labile groups in the polymer provide the necessary solubility change. The polymer without the acid labile group is soluble in an aqueous alkaline solution, but when protected with an acid labile group becomes insoluble. Examples of monomers that impart alkali solubility are acrylic acid, methacrylic acid, vinyl alcohol, hydroxystyrenes, vinyl monomers containing 1,1'2, 2',3,3'-hexafluoro-2-propanol, although any group that makes the polymer alkali soluble may be used. The hydrophilic functionalities can be protected with acid labile groups such as —(CO)O—R, —O—R, —O(CO)O—R, —C(CF$_3$)$_2$O—R, —C(CF$_3$)$_2$O(CO)O—R, and —C(CF$_3$)$_2$(COOR), where R is alkyl, cycloalkyl, substituted cycloalkyl, oxocyclohexyl, cyclic lactone, benzyl, silyl, alkyl silyl, substituted benzyl, alkoxy alkyl such as ethoxy ethyl or methoxy ethoxy ethyl, acetoxyalkoxy alkyl such as acetoxy ethoxy ethyl, tetrahydrofuranyl, menthyl, tetrahydropyranyl and mevalonic lactone. Examples of specific groups for R are t-butoxycarbonyl tricyclo(5.3.2.0)decanyl, 2-methyl-2-adamantyl, isobornyl, norbornyl, adamantyloxyethoxy ethyl, menthyl, tertiary butyl, tetrahydropyranyl and 3-oxocyclohexyl. Preferably R is tert-butyl, 3-hydroxy-1-adamantyl, 2-methyl-2-adamantyl, beta-(gamma-butyrolactonyl), or mevalonic lactone. Some of the preferred monomers are vinyl compounds with the above mentioned labile groups. It is within the scope of this invention that any acid labile group that can be cleaved with an acid may be attached to the polymer, which in the presence of an acid gives an alkali soluble polymer. The protected monomers may be polymerized to give homopolymers or with other unprotected monomers as required. Alternatively, an alkali soluble homopolymer or copolymer may be reacted with a compound, or compounds, which provide the acid labile group.

The polymer of the antireflective coating of the first embodiment of the invention contains at least one unit with an acid labile group and at least one unit with an absorbing chromophore. Examples of an absorbing chromophore are hydrocarbon aromatic moieties and heterocyclic aromatic moieties with from one to four separate or fused rings, where there are 3 to 10 atoms in each ring. Examples of monomers with absorbing chromophores that can be polymerized with the monomers containing the acid labile groups are vinyl compounds containing substituted and unsubstituted phenyl, substituted and unsubstituted anthracyl, substituted and unsubstituted phenanthryl, substituted and unsubstituted naphthyl, substituted and unsubstituted heterocyclic rings containing heteroatoms such as oxygen, nitrogen, sulfur, or combinations thereof, such as pyrrolidinyl, pyranyl, piperidinyl, acridinyl, quinolinyl. Other chromophores are described in U.S. Pat. No. 6,114,085, and in U.S. Pat. Nos. 5,652,297, 5,981,145, 6,187,506, 5,939,236, and 5,935,760, which may also be used, and are incorporated herein by reference. The preferred chromophores are vinyl compounds of substituted and unsubstituted phenyl, substituted and unsubstituted anthracyl, and substituted and unsubstituted naphthyl; and more preferred monomers are styrene, hydroxystyrene, acetoxystyrene, vinyl benzoate, vinyl 4-tert-butylbenzoate, ethylene glycol phenyl ether acrylate, phenoxypropyl acrylate, 2-(4-benzoyl-3-hydroxyphenoxy) ethyl acrylate, 2-hydroxy-3-phenoxypropyl acrylate, phenyl methacrylate, benzyl methacrylate, 9-anthracenylmethyl methacrylate, 9-vinylanthracene, 2-vinylnaphthalene. It is within the scope of this invention that any chromphore that absorbs at the appropriate exposure wavelength may be used alone or in combination with other chromophores. Thus a polymer may be synthesized by polymerizing monomers that contain an acid labile group with monomers that contain an absorbing chromophore. Alternatively, the alkali soluble polymer may be reacted with compounds that provide the acid labile group and compounds that provide the absorbing chromophore. The mole % of the acid labile unit in the final polymer can range from 5 to 95, and the mole % of the absorbing chromophore unit in the final polymer can range from 5 to 95. It is also within the scope of this invention that the acid labile group is attached to the absorbing chrormphore or that the chromophore is attached to the acid labile group, for example the monomers may be $CH_2$=CHX—Ar—(CO)$_n$O—R (n=0–1), $CH_2$=CHX—Ar—OC(O)O—R, (CH)=CHX—Ar—C(CF$_3$)$_2$O—R, $CH_2$=CHX—Ar—C(CF$_3$)$_2$O(CO)O—R, $CH_2$=CHX—Ar—C(CF$_3$)$_2$(COOR), $CH_2$=CHX—C(O)O—Ar—OC(O)—R, $CH_2$=CHX—CON(X)—Ar—O—R, and vinyl compounds containing —(CO)O—R—Ar, —OC(O)O—R—Ar, —C(CF$_3$)$_2$O—R—Ar, —C(CF$_3$)$_2$O(CO)O—R—Ar, C(CF$_3$)$_2$(COOR—Ar), where X is H or alkyl, Ar is substituted and unsubstituted phenyl such as phenyl or benzyl, substituted and unsubstituted anthracyl such as anthracylmethyl, substituted and unsubstituted phenanthryl, substituted and unsubstituted naphthyl, substituted and unsubstituted heterocyclic aromatic rings containing heteroatoms such as oxygen, nitrogen, sulfur, or combinations thereof, such as pyrrolidinyl, pyranyl, piperidinyl, acridinyl, quinolinyl, and R is alkyl, cycloalkyl, substituted cycloalkyl, oxocyclohexyl, cyclic lactone, benzyl, substituted benzyl, alkoxy alkyl, such as ethoxy ethyl or methoxy ethoxy ethyl, acetoxy ethoxy ethyl, tetrahydrofuranyl, menthyl, tetrahydropyranyl, mevalonic lactone. Examples of specific groups for R are t-butoxycarbonyl tricyclo(5.3.2.0)decanyl, 2-methyl-2-adamantol, isobornyl, norbornyl, adamantyloxyethoxy ethyl, menthyl, tertiary butyl, tetrahydropyranyl, 3-oxocyclohexyl.

Other than the unit containing the acid labile group and the absorbing chrormphore, the polymer may contain other nonabsorbing monomeric units, such units may provide other desirable properties. Examples of the third monomer are —CR$_1$R$_2$—CR$_3$R$_4$—, where R$_1$ to R$_4$ are independently H, (C$_1$–C$_{10}$)alkyl, (C$_1$–C$_{10}$)alkoxy, nitro, halide, cyano, alkylaryl, alkenyl, dicyanovinyl, SO$_2$CF$_3$, COOZ, SO$_3$Z, COZ, OZ, NZ$_2$, SZ, SO$_2$Z, NHCOZ, SO$_2$NZ$_2$, where Z is H, or (C$_1$–C$_{10}$)alkyl, hydroxy(C$_1$–C$_{10}$)alkyl, (C$_1$–C$_{10}$)alkylOCOCH$_2$COCH$_3$, or R$_2$ and R$_4$ combine to form a cyclic group such as anhydride, pyridine, or pyrrolidone, or R$_1$ to R$_3$ are independently H, (C$_1$–C$_{10}$)alkyl, (C$_1$–C$_{10}$) alkoxy and R$_4$ is a hydrophilic group. Examples of the hydrophilic group, are given here but are not limited to these: O(CH$_2$)$_2$OH, O(CH$_2$)$_2$O(CH$_2$)OH, (CH$_2$)$_n$OH (where n=0–4), COO(C$_1$–C$_4$)alkyl, COOX and SO$_3$X (where X is H, ammonium, alkyl ammonium). Other hydrophilic vinyl monomers that can be used to form the polymer are acrylic acid, methacrylic acid, vinyl alcohol, maleic anhydride, maleic acid, maleimide, N-methyl maleimide, N-hydroxymethyl acrylamide and N-vinyl pyrrolidinone. Other monomers may be methyl methacrylate, butyl methacrylate, hydroxyethyl methacrylate and hydroxypropyl methacrylate.

Examples of monomers containing acid labile groups that can be used in the polymers are methacrylate ester of methyladamantane, methacrylate ester of mevalonic lactone, 3-hydroxy-1-adamantyl methacrylate, methacrylate ester of beta-hydroxy-gamma-butyrolactone, t-butyl norbornyl carboxylate, t-butyl methyl adamantyl methacryate, methyl adamantyl acrylate, t-butyl acrylate and t-butyl methacrylate; t-butoxy carbonyl oxy vinyl benzene, benzyl oxy carbonyl oxy vinyl benzene; ethoxy ethyl oxy vinyl benzene; trimethyl silyl ether of vinyl phenol, and 2-tris (trimethylsilyl)silyl ethyl ester of methyl methacrylate.

The monomers containing an absorbing chromophore and are suitable for this invention are hydroxystyrene, styrene, acetoxystyrene, benzyl methacrylate, N-methyl maleimide, vinyl benzoate, vinyl 4-tert-butylbenzoate, ethylene glycol phenyl ether acrylate, phenoxypropyl acrylate, 2-hydroxy-3-phenoxypropyl acrylate, phenyl methacrylate, benzyl methacrylate, 9-anthracenylmethyl methacrylate, 9-vinylanthracene, 2-vinylnaphthalene, N-vinylphthalimide, N-(3-hydroxy)phenyl methacrylamide, N-(3-hydroxy-4-hydroxycarbonylphenylazo)phenyl methacrylamide, N-(3-hydroxyl-4-ethoxycarbonylphenylazo)phenyl methacrylamide, N-(2,4-dinitrophenylaminophenyl) maleimide, 3-(4-acetoaminophenyl)azo-4-hydroxystyrene, 3-(4-ethoxycarbonylphenyl)azo-acetoacetoxy ethyl methacrylate, 3-(4-hydroxyphenyl)azo-acetoacetoxy ethyl methacrylate, tetrahydroammonium sulfate salt of 3-(4-sulfophenyl)azoacetoacetoxy ethyl methacrylate.

The second embodiment of the present invention relates to an antireflective coating composition comprising a polymer with at least one unit with an acid labile group, a dye and a photoacid generator. The polymer containing the acid labile groups are of the same scope as previously described. In this particular invention the absorption necessary for the antireflective coating is provided not by the unit in the polymer, but by the incorporation of an additive that absorbs at the exposure wavelength. This dye may be monomeric, polymeric or mixtures of both. Examples of absorbing groups that may be contained in an additive absorbing compound are substituted and unsubstituted phenyl, substituted and unsubstituted anthracyl, substituted and unsubstituted phenanthryl, substituted and unsubstituted naphthyl, substituted and unsubstituted heterocyclic rings containing heteroatoms such as oxygen, nitrogen, sulfur, or combinations thereof, such as pyrrolidinyl, pyranyl, piperidinyl, acridinyl, quinolinyl. Absorbing polymeric dyes that may be used are polymers of the absorbing moieties listed above, where the polymer backbone may be polyesters, polyimides, polysulfones and polycarbonates. Some of the preferred dyes are copolymers of hydroxystyrene and methyl methacrylate, such as disclosed in U.S. Pat. No. 6,114,085, and azo polymeric and monomeric dyes, such as disclosed in U.S. Pat. Nos. 5,652,297, 5,763,135, 5,981,145, 6,187,506, 5,939,236, and 5,935,760, all of which are incorporated herein by reference. Examples of dyes are monomers or polymers of triphenylphenol, 2-hydroxyfluorene, 9-anthracenemethanol, 2-methylphenanthrene, 2-naphthalene ethanol, 2-naphthyl-beta-d-galactopyranoside hydride, hydroxystyrene, styrene, acetoxystyrene, benzyl methacrylate, N-methyl maleimide, vinyl benzoate, vinyl 4-tert-butylbenzoate, ethylene glycol phenyl ether acrylate, phenoxypropyl acrylate, benzyl mevalonic lactone ester of maleic acid, 2-hydroxy-3-phenoxypropyl acrylate, phenyl methacrylate, benzyl methacrylate, 9-anthracenylmethyl methacrylate, 9-vinylanthracene, 2-vinylnaphthalene, N-vinylphthalimide, N-(3-hydroxy)phenyl methacrylamide, N-(3-hydroxy-4-hydroxycarbonylphenylazo)phenyl methacrylamide, N-(3-hydroxyl-4-ethoxycarbonylphenylazo)phenyl methacrylamide, N-(2,4-dinitrophenylaminophenyl) maleimide, 3-(4-acetoaminophenyl)azo-4-hydroxystyrene, 3-(4-ethoxycarbonylphenyl)azo-acetoacetoxy ethyl methacrylate, 3-(4-hydroxyphenyl)azo-acetoacetoxy ethyl methacrylate, tetrahydroammonium sulfate salt of 3-(4-sulfophenyl)azoacetoacetoxy ethyl methacrylate.

The polymer of the second embodiment containing the acid labile unit may also contain other nonabsorbing monomeric units as described in the first embodiment. Examples of the polymer useful for this embodiment and containing the acid labile group are copolymers of 2-methyl-2-adamantyl methacrylate, mevalonic lactone methacrylate, 3-hydroxy-1-adamantyl methacrylate, methacrylate ester of beta-hydroxy-gamma-butyrolactone, t-butyl norbornyl carboxylate, t-butyl methyl adamantyl methacryate, methyl adamantyl acrylate, t-butyl acrylate and t-butyl methacrylate; t-butoxy carbonyl oxy vinyl benzene, benzyl oxy carbonyl oxy vinyl benzene; ethoxy ethyl oxy vinyl benzene; trimethyl silyl ether of vinyl phenol, and 2-tris (trimethylsilyl)silyl ethyl ester of methyl methacrylate, with methyl methacrylate, butyl methacrylate, acrylic acid, methacrylic acid, vinyl alcohol, maleic anhydride, N-vinyl pyrrolidinone, maleimide, N-methyl maleimide, hydroxyethyl methacrylate, hydroxypropyl methacrylate, and N-(hydroxymethyl)acrylamide.

In a third embodiment of the invention the antireflective coating composition comprises a polymer with at least one unit with an acid labile group. The polymer containing the acid labile groups are of the same scope as described previously. There is effectively no photoacid generator in the composition. The acid labile group in the antireflective coating is deprotected by heating the bilevel system after the exposure step so that acid from the photoresist diffuses to cause the deprotection in the antireflective coating. In such cases, particularly thin coatings of the antireflective coating are preferred. Particularly preferred are coatings of less than 70 nm. Any of the polymeric or monomeric dyes described above may be used in the composition or the polymer may contain a unit with the absorbing chromophore described previously.

The polymers of this invention may be synthesized using any known method of polymerization, such as ring-opening metathesis, free-radical polymerization, condensation polymerization, using metal organic catalysts, or anionic or cationic copolymerization techniques. The polymer may be synthesized using solution, emulsion, bulk, suspension polymerization, or the like. The polymers of this invention are polymerized to give a polymer with a weight average molecular weight from about 1,000 to about 1,000,000, preferably from about 2,000 to about 80,000, more preferably from about 6,000 to about 50,000. When the weight average molecular weight is below 1,000, then good film forming properties are not obtained for the antireflective coating and when the weight average molecular weight is too high, then properties such as solubility, storage stability and the like may be compromised. The polydispersity(Mw/Mn) of the free-radical polymers, where Mw is the weight average molecular weight and Mn is the number average molecular weight, can range from 1.0 to 10.0, where the molecular weights of the polymer may be determined by gel permeation chromatography.

The solvent for the antireflective coating is chosen such that it can dissolve all the solid components of the antireflective coating, and also can be removed during the bake step so that the resulting coating is not soluble in the coating solvent of the photoresist. Furthermore, to retain the integrity of the antireflective coating, the polymer of the antireflective coating is also not soluble in the solvent of the top photoresist. Such requirements prevent, or minimize, intermixing of the antireflecting coating layer with the photoresist layer. Typically propyleneglycolmonomethyl ether acetate and ethyl lactate are the preferred solvents for the top photoresist. Examples of suitable solvents for the antireflective coating composition are cyclohexanone, cyclopentanone, anisole, 2-heptanone, ethyl lactate, propylene glycol monomethyl ether acetate, propylene glycol monomethyl ether, butyl acetate, gamma butyroacetate, ethyl cellosolve acetate, methyl cellosolve acetate, methyl 3-methoxypropionate, ethyl pyruvate, 2-methoxybutyl acetate, 2-methoxyethyl ether, but ethyl lactate, propylene glycol monomethyl ether acetate, propylene glycol monomethyl ether or mixtures thereof are preferred. Solvents with a lower degree of toxicity and good coating and solubility properties are generally preferred.

Typical antireflective coating compositions of the present invention may comprise up to about 15 percent by weight of the solids, preferably less than 8 percent, based on the total weight of the coating composition. The solids may comprise from 0 to 25 weight percent of the photoacid generator, 50 to 99 weight percent of polymer and optionally 5 to 60 weight percent of the dye, based on the total solids content of the antireflective coating composition. The solid components are dissolved in the solvent, or mixtures of solvents, and filtered to remove impurities. The components of the antireflective coating may also be treated by techniques such as passing through an ion exchange column, filtration, and extraction process, to improve the quality of the product.

Other components may be added to the three embodiments described in the application in order to enhance the performance of the coating, e.g. lower alcohols, dyes, surface leveling agents, adhesion promoters, antifoaming agents, etc. These additives may be present at up to 30 weight percent level. Other polymers, such as, novolaks, polyhydroxystyrene, polymethylmethacrylate and polyarylates, may be added to the composition, providing the performance is not negatively impacted. Preferably the amount of this polymer is kept below 50 weight % of the total solids of the composition, more preferably 35 weight %, and even more preferably below 20 weight %. Bases may also be added to the composition to enhance stability. Both photobases and nonphotobases are known additives. Examples of bases are amines, ammonium hydroxide, and photosensitive bases. Particularly preferred bases are tetrabutylammonium hydroxide, triethanolamine, diethanol amine, trioctylamine, n-octylamine, trimethylsulfonium hydroxide, triphenylsulfonium hydroxide, bis(t-butylphenyl)iodonium cyclamate and tris(tert-butylphenyl) sulfonium cyclamate.

The absorption parameter (k) of the novel composition ranges from about 0.1 to about 1.0, preferably from about 0.15 to about 0.7 as measured using ellipsometry. The refractive index (n) of the antireflective coating is also optimized. The exact values of the optimum ranges for k and n are dependent on the exposure wavelength used and the type of application. Typically for 193 nm the preferred range for k is 0.2 to 0.75, for 248 nm the preferred range for k is 0.25 to 0.8, and for 365 nm the preferred range is from 0.2 to 0.8. The thickness of the antireflective coating is less than the thickness of the top photoresist. Preferably the film thickness of the antireflective coating is less than the value of (wavelength of exposure/refractive index), and more preferably it is less than the value of (wavelength of exposure/2 times refractive index), where the refractive index is that of the antireflective coating and can be measured with an ellipsometer. The optimum film thickness of the antireflective coating is determined by the exposure wavelength, refractive indices of the antireflective coating and of the photoresist, and absorption characteristics of the top and bottom coatings. Since the bottom antireflective coating must be removed by exposure and development steps, the optimum film thickness is determined by avoiding the optical nodes where no light absorption is present in the antireflective coating.

The antireflective coating composition is coated on the substrate using techniques well known to those skilled in the art, such as dipping, spin coating or spraying. Various substrates known in the art may be used, such as those that are planar, have topography or have holes. The film thickness of the antireflective coating ranges from about 20 nm to about 300 nm. The optimum film thickness is determined, as is well known in the art, to be where good lithographic properties are obtained, especially where no standing waves are observed in the photoresist. It has been unexpectedly found that for this novel composition very thin coatings can be used due to the excellent absorption and refractive index properties of the film. The coating is further heated on a hot plate or convection oven for a sufficient length of time to remove any residual solvent, and thus insolubilizing the antireflective coating to prevent intermixing between the antireflective coating and the photoresist layer. The preferred range of temperature is from about 40° C. to about 240° C., more preferably from about 80° C. to about 150° C. The antireflective coating is also insoluble at this stage in the alkaline developing solution.

Positive photoresists, which are developed with aqueous alkaline solutions, are useful for the present invention, provided the photoactive compounds in the photoresist and the antireflective coating absorb at the same exposure wavelength used for the imaging process for the photoresist. Positive-working photoresist compositions are exposed image-wise to radiation, those areas of the photoresist composition exposed to the radiation become more soluble to the developer solution (e.g. a rearrangement reaction occurs) while those areas not exposed remain relatively insoluble to the developer solution. Thus, treatment of an exposed positive-working photoresist with the developer causes removal of the exposed areas of the coating and the formation of a positive image in the photoresist coating. Photoresist resolution is defined as the smallest feature which the resist composition can transfer from the photomask to the substrate with a high degree of image edge acuity after exposure and development. In many manufacturing applications today, resist resolution on the order of less than one micron are necessary. In addition, it is almost always desirable that the developed photoresist wall profiles be near vertical relative to the substrate. Such demarcations between developed and undeveloped areas of the resist coating translate into accurate pattern transfer of the mask image onto the substrate. This becomes even more critical as the drive toward miniaturization reduces the critical dimensions on the devices.

Positive-acting photoresists comprising novolak resins and quinone-diazide compounds as photoactive compounds are well known in the art Novolak resins are typically produced by condensing formaldehyde and one or more multi-substituted phenols, in the presence of an acid catalyst, such as oxalic acid. Photoactive compounds are generally obtained by reacting multihydroxyphenolic compounds with naphthoquinone diazide acids or their derivatives. The sensitivity of these types of resists typically ranges from about 300 nm to 440 nm.

Photoresists sensitive to short wavelengths, between about 180 nm and about 300 nm can also be used. These photoresists normally comprise polyhydroxystyrene or substituted polyhydroxystyrene derivatives, a photoactive compound, and optionally a solubility inhibitor. The following references exemplify the types of photoresists used and are incorporated herein by reference, U.S. Pat. Nos. 4,491, 628, 5,069,997 and 5,350,660. Particularly preferred for 193 nm and 157 nm exposure are photoresists comprising non-aromatic polymers, a photoacid generator, optionally a solubility inhibitor, and solvent. Photoresists sensitive at 193 nm that are known in the prior art are described in the following references and incorporated herein, EP 794458, WO 97/33198 and U.S. Pat. No. 5,585,219, although any photoresist sensitive at 193 nm may be used on top of the antireflective composition of this invention.

A film of photoresist is then coated on top of the antireflective coating and baked to substantially remove the photoresist solvent. The photoresist and the antireflective coating bilevel system is then imagewise exposed. In a subsequent heating step the acid generated during exposure reacts to deprotect the polymer and thus render alkali soluble in the developing solution. The temperature for the postexposure bake step can range from 40° C. to 200° C., preferably from 80° C. to 160° C. In some instances, it is possible to avoid the postexposure bake, since for certain chemistries, such as acetal acid labile groups, deprotection proceeds at room temperature. The bilevel system is then developed in an aqueous developer to remove the treated photoresist and the antireflective coating. The developer is preferably an aqueous alkaline solution comprising, for example, tetramethyl ammonium hydroxide. The developer may further comprise additives, such as surfactants, polymers, isopropanol, ethanol, etc. The process of coating and imaging photoresist coatings and antireflective coatings is well known to those skilled in the art and is optimized for the specific type of photoresist and antireflective coating combination used. The imaged bilevel system can then be processed further as required by the manufacturing process of integrated circuits, for example metal deposition and etching.

The fourth embodiment relates to the process, as described above, of forming a positive image comprising;

a) providing a coating of the bottom photoimageable and alkali developable antireflective coating composition on a substrate;

b) providing a coating of a top photoresist layer;

c) imagewise exposing the top and bottom layer to actinic radiation of same wavelength;

d) postexposure baking the substrate; and, e) developing the top and bottom layer with an aqueous alkaline solution.

Each of the documents referred to above are incorporated herein by reference in its entirety, for all purposes. The following specific examples will provide detailed illustrations of the methods of producing and utilizing compositions of the, present invention. These examples are not intended, however, to limit or restrict the scope of the invention in any way and should not be construed as providing conditions, parameters or values which must be utilized exclusively in order to practice the present invention.

EXAMPLES

Example 1A

To a 250 ml, 4 neck flask equipped with a condenser, a thermometer, a nitrogen gas inlet and a mechanical stirrer, were added N-methyl maleimide (5 g), methacrylate ester of mevalonic lactone (MLMA) (26 g), methacrylate ester of methyladamantane (MADMA) (3 g), azoisobutyinitrile (AIBN) (5.2 g) and tetrahydrofuran (THF) (60 g). A solution was obtained and degassed for 10 minutes. The reaction was refluxed for 4 hours and then drowned into 600 ml of hexane. The precipitated polymer was filtered and dried.

A 4 weight % solution of the above polymer was made in cyclopentanone and a 4 inch unprimed silicon wafer was coated. The wafer was then soft baked at 110° C. for 60 seconds. To check the solvent resistance of the polymer coating, first a drop of propylene glycol monomethyl ether acetate (PGMEA) was placed on the top of the wafer for 60 seconds and blown dry with nitrogen. No dissolution of the antireflective coating was observed. Then a drop of water was placed on the top of the coating for 30 seconds to simulate wafer washing and then blown dry with nitrogen. Again the coating was not effected. Finally a drop of AZ® 300 MIF Developer (a 2.38% tetramethyl ammonium hydroxide aqueous solution, available from Clariant Corp. Somerville, N.J.) was placed on the coating for 30 seconds and then washed off with deionized water (DI) water and wafer dried with nitrogen. There was no indication of solubility of the polymer in all cases.

Example 1B

To the polymer (0.8 g) from Example 1A prepared above, was added triphenylsulfonium nonaflate (0.016 g), cyclopentanone (20 g) polymethyl methacrylate-co-(acetoaminophenylazo)hydroxystyrene (0.2 g) (available from Clariant Corp.) and 0.13 g of a 1% triethanolamine solution in cyclopentanone. The solution (4% solids) was mixed and filtered through a 1.0 μm filter to give a bottom antireflective coating solution.

A silicon wafer was coated first with 700 Å of the bottom antireflective coating (B.A.R.C.) solution from above and softbaked (SB) at 110° C. for 60 seconds. Next the B.A.R.C. coated wafer was coated with 4340 Å of AZ® EXP AX2020P photoresist (available from Clariant Corp.) and baked at 110° C./60 seconds. The coated wafer was exposed using an ISI 193 nm ministepper. The exposed wafer had a post exposure bake (PEB) of 90 seconds at 130° C. The wafer was puddle developed with AZ® 300 MIF Developer for 30 seconds. The pictures taken by scanning electron microscope (SEM), showed both the photoresist and B.A.R.C. were developed at a dose of 17 mJ/cm$^2$ for 0.19 μm dense lines. The B.A.R.C. coating also gave a refractive index and absorption at 193 nm for n and k of 1.65 and 0.12 respectively as measured by a J. A. Woollam WVASE 32™ Ellipsometer.

Example 2A

To a 250 ml, 4 neck flask equipped with a condenser, a thermometer, nitrogen gas inlet and a mechanical stirrer, were added styrene (1.6 g), MLMA (18.4 g), AIBN (3 g) and THF (50 g). A solution was obtained and degassed for 10 minutes. The reaction was refluxed for 4.5 hours and then drowned into 600 ml of hexane. The precipitated polymer was filtered and dried.

Example 2B

To the polymer (0.41 g) from Example 2A were added triphenylsulfonium nonaflate (0.06 g), cyclopentanone (20 g), 1200 ppm of FC 4430 (available from 3M Corp.), and 0.6 g of a 1% triethanolamine solution in THF. The (2.58% solids) solution was mixed and filtered through a 0.1 μm filter to give a B.A.R.C. solution.

A silicon wafer was coated first with 600 Å of the B.A.R.C. prepared above with a SB of 110° C./60 seconds. Next the B.A.R.C. coated wafer was coated with 4670 Å of AZ® EXP AX2020P photoresist using a SB of 110° C./60 seconds. An ISI 193 nm ministepper was used for exposure through a mask. The exposed wafer had a PEB of 90 seconds at 130° C., followed by a 30-second puddle development using AZ® 300 MIF Developer. The SEM results showed clearly that both the B.A.R.C. and photoresist were developed at a dose of 23.5 mJ/cm2 for 0.18 µm dense lines. The B.A.R.C. coating also gave a refractive index and absorption at 193 nm for n and k of 1.70 and 0.32 respectively as measured by a J. A. Woollam WVASE 32™ Ellipsometer.

Comparative Example 3

A silicon wafer was coated first with 3300 Å of AZ® EXP AX2020P photoresist using a SB of 110° C./60 seconds. An ISI 193 nm ministepper was used for imagewise exposure. The exposed wafer had a PEB of 90 seconds at 130° C. followed by a 30 second puddle development using of AZ® 300 MIF Developer. The SEM dearly showed more standing waves for the photoresist in comparison to Example 2B.

Example 4A

To a 250 ml, 4 neck flask equipped with a condenser, a thermometer, a nitrogen gas inlet and a mechanical stirrer were added the methacrylate ester of 9-anthracene methanol (AMMA) (6.4 g), MLMA (8.6 g), AIBN (3 g) and cyclopentanone (40 g). A solution was obtained and degassed for 10 minutes. The reaction was refluxed for 4.5 hours and then drowned into 600 ml of hexane. The precipitated polymer was filtered and dried.

Example 4B

To the polymer (0.26 g) from Example 4A was added triphenylsulfonium nonaflate (0.016 g), FC-4430 (0.01 g) and 9.73 g of ethyl lactate. The (2.6% solids) solution was mixed and filtered through a 0.1 µm filter.

A silicon wafer was coated first with 600 Å of the prepared B.A.R.C. solution and softbaked at 110° C./60 seconds. Next the B.A.R.C. coated wafer was coated with 6310 Å of AZ® DX5200P photoresist (a hybrid acetal resist available from Clariant Corp.) using a bake of 90° C./60 second. The coated wafer was imagewise exposed using an ASML300 DUV Stepper (0.63 NA). The exposed wafer was given a PEB of 60 seconds at 120° C., followed by a puddle development of 60 seconds with AZ® 300 MIF Developer. The SEM results showed that the B.A.R.C. cleared down to the substrate with a dose of 20 mJ/cm2. The B.A.R.C. coating also gave a refractive index and absorption at 248 nm for n and k of 1.45 and 0.38 respectively as measured by a J. A. Woollam WVASE 32 TM Ellipsometer.

Example 5A

To a 250 ml, 4 neck flask equipped with a condenser, thermometer, gas inlet and a mechanical stirrer were added, MLMA (20.0 g), AIBN (3 g) and THF (40 g). A solution was obtained and degassed for 10 minutes. The reaction was refluxed for 4.5 hours and then drowned into 600 ml of hexane. The precipitated polymer was filtered and dried.

Example 6

To a 250 ml, 4 neck flask equipped with a condenser, thermometer, nitrogen gas inlet, and a mechanical stirrer were added benzyl methacrylate (6.5 g), methacrylate ester of mevalonic lactone (MLMA) (13.5 g), azoisobutylnitrile (AIBN) (3 g) and tetrahydrofuran (THF) (50 g). A solution was obtained and degassed for 10 minutes. The reaction was refluxed for 6 hours and then drowned into 600 ml of hexane. The precipitated polymer was filtered and dried. The polymer was next dissolved in 60 g of cyclopentanone and then slowly added to 600 ml of methanol to reprecipitate the polymer. The polymer was filtered, rinsed and dried. The reprecipitated polymer was redissolved in 60 g of cyclopentanone and then precipitated again into 600 ml of methanol.

Example 7

To the polymer (0.346 g) from Example 6 were added triphenylsulfonium nonaflate (0.0034 g), 0.0008 g of triphenylsulfonium hydroxide, FC-4330 (0.01 g) and 9.64 g of ethyl lactate. The (3.85% solids) solution was mixed and filtered through a 0.1 µm filter.

A silicon wafer was coated first with 600 Å of the prepared B.A.R.C. solution and softbaked at 110° C./60 seconds. Next the B.A.R.C. coated wafer was coated with 3300 Å of AZ® EXP AX2020P photoresist using a bake of 130° C./60 second. The coated wafer was imagewise exposed using an ISI 193 nm ministepper. The exposed wafer was given a PEB of 60 seconds at 120° C., followed by a puddle development of 60 seconds with AZ® 300 MIF Developer. The SEM results show that for 0.18 µm lines, 23 mJ/cm$^2$ was required to clear these isolated lines. The B.A.R.C. coating also gave a refractive index and absorption at 193 nm for n and k of 1.85 and 0.34 respectively as measured by a J. A. Woollam WVASE 32™ Ellipsometer.

Example 8

A B.A.R.C. solution was prepared as follows. To 0.177 g of the polymer prepared above in Example 6 were added 0.0027 g of triphenylsulfonium nonaflate, 0.00023 g of tridecylamine, FC-4430 (0.01 g) and 9.82 g of ethyl lactate. The resulting (4.0% solids) solution was filtered through a 0.1 µm filter.

A silicon wafer was coated with 300 Å of the B.A.R.C. solution prepared above and softbaked at 110° C./60 seconds. Next the B.A.R.C. coated wafer was coated with 3300 Å of AZ® EXP AX2020P photoresist using a SB of 130° C./60 seconds. The coated wafer was imagewise exposed using an ISI 193 nm ministepper. The exposed wafer had a PEB of 60 seconds at 120° C., followed by a puddle development of 60 second with AZ® 300 MIF Developer.

The SEM results showed that 11 mJ/cm$^2$ was required to cleanly open 0.18 µm isolated lines. The dense lines (1:1) cleared at 17 mJ/cm$^2$ with clean well shaped dense 1:1 lines. The B.A.R.C. coating also gave a refractive index and absorption at 193 nm for n and k of 1.85 and 0.34 respectively as measured by a J. A. Woollam WVASE 32™ Ellipsometer.

Example 9

A B.A.R.C. solution was prepared as follows. To 0.177 g of the polymer prepared above in Example 6 was added 0.0027 g of triphenylsulfonium nonaflate, 0.00028 g of adamantamine, FC-4430 (0.01 g) and 9.82 g of ethyl lactate. The resulting (4.0% solids) solution was filtered through a 0.1 µm filter.

A silicon wafer was coated with 300 Å of the B.A.R.C. solution prepared above using a SB of 110° C./60 seconds. Next the B.A.R.C. coated wafer was coated with 3300 Å of AZ® EXP AX2020P photoresist using a SB of 130° C./60 seconds. The coated wafer was imagewise exposed using an ISI 193 nm ministepper. The exposed wafer had a PEB of 60 seconds at 120° C., followed by 60 second puddle development with AZ® 300 MIF Developer.

The SEM results show that 13 mJ/cm$^2$ was required to cleanly open 0.18 µm isolated lines. The dense lines (1:1) cleared at 21 mJ/cm$^2$. The B.A.R.C. coating also gave a refractive index and absorption at 193 nm for n and k of 1.85 and 0.34 respectively as measured by a J. A. Woollam WVASE 32™ Ellipsometer.

Example 10

A B.A.R.C. solution was prepared as follows. To 0.177 g of the polymer prepared above in Example 6 was added 0.0027 g of triphenylsulfonium nonaflate, 0.00027 g of trimethylsulfonium hydroxide, FC-4430 (0.01 g) and 9.82 g of ethyl lactate. The resulting (4.0% solids) solution was filtered through a 0.1 μm filter.

A silicon wafer was coated with 300 Å of the B.A.R.C. solution prepared above using a SB of 110° C./60 seconds. Next the B.A.R.C. coated wafer was coated with 3300 Å of AZ® EXP AX2020P photoresist using a SB of 130° C./60 seconds. The coated wafer was exposed using an ISI 193 nm ministepper. The exposed wafer was given a PEB of 60 seconds at 120° C., followed by 60 second puddle development with AZ® 300 MIF Developer.

The SEM results show that 15 mJ/cm$^2$ was required to cleanly open 0.18 μm isolated lines. The dense lines were also open at 15 mJ/cm$^2$. The B.A.R.C. coating also gave a refractive index and absorption at 193 nm for n and k of 1.85 and 0.34 respectively as measured by a J. A. Woollam WVASE 32™ Ellipsometer.

What is claimed is:

1. A positive bottom photoimageable antireflective coating composition which is capable of being developed in an aqueous alkaline developer and which is coated below a positive photoresist, where the antireflective coating composition comprises a photoacid generator and a polymer comprising at least one unit with an acid labile group and at least one unit with an absorbing chromophore, further where the absorbing chromochore is selected from hydrocarbon aromatic moieties with one ring and heterocyclic aromatic moieties with one ring.

2. The composition according to claim 1 where the acid labile group is selected from —(CO)O—R, —O—R, —O(CO)O—R, —C(CF$_3$)$_2$O—R, —C(CF$_3$)$_2$O(CO)O—R and —C(CF$_3$)$_2$(COOR), where R is alkyl, cycloalkyl, substituted cycloalkyl, oxocyclohexyl, cyclic lactone, benzyl, substituted benzyl, alkoxy alkyl, acetoxy alkoxyoxy alkyl, tetrahydrofuranyl, methyl adamantyl, menthyl, tetrahydropyranyl and mevalonic lactone.

3. The composition according to claim 1 where the absorbing chromophore is selected from substituted and unsubstituted phenyl, and substituted and unsubstituted heterocyclic aromatic rings containing heteroatoms selected from oxygen, nitrogen, sulfur, and combinations thereof.

4. The composition according to claim 1 where the polymer is selected from copolymers of 2-methyl-2-adamantyl methacrylate, mevalonic lactone methacrylate, 3-hydroxy-1-adamentyl methacrylate, methacrylate ester of beta-hydroxy-gamma-butyrolactone, t-butyl nornyl carboxylate, t-butyl methyl adamantyl methacryate, t-butyl acrylate and t-butyl methacrylate; t-butoxy carbonyl oxy vinyl benzene, benzyl oxy carbonyl oxy vinyl benzene; ethoxy ethyl oxy vinyl benzene; trimethyl silyl ether of vinyl phenol, and 2-tris(trimethylsilyl)silyl ethyl ester of methyl methacrylate, with acrylic acid, methacrylic acid, vinyl alcohol, maleic anhydride, maleic acid, maleimide, N-methyl maleimide, N-hydroxymethyl acrylamide, N-vinyl pyrrolidinone, methyl methacrylate, butyl methacrylate, hydroxyethyl methacrylate and hydroxypropyl methacrylate, hydroxystyrene, styrene, acetoxystyrene, benzyl methacrylate, N-methyl maleimide, vinyl berizoate, vinyl 4-tert-butylbenzoate, ethylene glycol phenyl ether acrylate, phenoxypropyl acrylate, 2-hydroxy-3-phenoxypropyl acrylate, phenyl methacrylate, benzyl methacrylate, N-vinylphthalimide, N-(3-hydroxy)phenyl methacrylamide, N-(3-hydroxy-4-hydroxycarbonylphenylazo)phenyl methacrylamide, N-(3-hydroxyl-4-ethoxycarbonylphenylazo)phenyl methacrylamide, N-(2,4-dinitrophenylaminophenyl) maleimide, 3-(4acetoaminophenyl)azo-4-hydroxystyrene, 3-(4-ethoxycorbonylphenyl)azo-acetoacetoxy ethyl methacrylate, 3-(4-hydroxyphenyl)azo-acetoacetoxy ethyl methacrylate, tetrahydroammonium sulfate salt of 3-(4-sulfophenyl)azoacetoacetoxy ethyl methacrylate.

5. The composition according to claim 1 where the antireflective layer has a k value in the range of 0.1 to 1.0.

6. The composition according to claim 1 where the photoacid generator is sensitive in the range of 450 nm to 100 nm.

7. The composition according to claim 6 where the photoacid generator is sensitive at wavelengths selected from 436 nm, 365 nm, 248 nm, 193 nm and 157 nm.

8. A process for forming a positive image comprising:

a) providing a coating of the bottom photoimageable antireflective coating composition of claim 1 on a substrate;

b) providing a coating of a top photoresist layer over the bottom coating;

c) imagewise exposing the top and bottom layers to actinic radiation of same wavelength;

d) postexposure baking the substrate; and, e) developing the top and bottom layers with an aqueous alkaline solution.

9. The process according to claim 8 where the antireflective coating is insoluble in the aqueous alkaline solution prior to the exposing step and becomes soluble prior to the developing step.

10. The process according to claim 8 where the aqueous alkaline solution comprises tetramethylammonium hydroxide.

11. The process according to claim 10 where the aqueous alkaline solution further comprises a surfactant.

12. A positive bottom photoimageable antireflective coating composition which is capable of being developed in an aqueous alkaline developer and which is coated below a positive photoresist, where the antireflective coating composition comprises a photoacid generator and a polymer comprising at least one unit with an acid labile group and an absorbing chromophore.

13. The composition of claim 12 where the acid labile group is selected from —(CO)O—R, —O—R, —O(CO)O—R, —C(CF$_3$)$_2$O—R, —C(CF$_3$)$_2$O(CO)O—R and —C(CF$_3$)$_2$(COOR), where R is alkyl, cycloalkyl, substituted cycloalkyl, oxocyclohexyl, cyclic lactone, benzyl, substituted benzyl, alkoxy alkyl, acetoxy alkoxyoxy alkyl, tetrahydrofuranyl, methyl adamantyl, menthyl, tetrahydropyranyl and mevalonic lactone.

14. The composition according to claim 12 where the absorbing chromophore is selected from compounds containing hydrocarbon aromatic rings, substituted and unsubstituted phenyl, substituted and unsubstituted anthracyl, substituted and unsubstituted phenanthryl, substituted and unsubstituted naphthyl, and substituted and unsubstituted heterocyclic aromatic rings containing heteroatoms selected from oxygen, nitrogen, sulfur, and combinations thereof.

15. The composition according to claim 12 where the antireflective layer has a k value in the range of 0.1 to 1.0.

16. The composition according to claim 12 where the photoacid generator is sensitive in the range of 450 nm to 100 nm.

17. The composition according to claim 16 where the photoacid generator is sensitive at wavelengths selected from 436 nm, 365 nm, 248 nm, 193 nm and 157 nm.

18. A process for forming a positive image comprising:
   b) providing a coating of the bottom photoimageable antireflective coating composition of claim 12 on a substrate;
   b) providing a coating of a top photoresist layer over the bottom coating;
   c) imagewise exposing the top and bottom layers to actinic radiation of same wavelength;
   f) postexposure baking the substrate; and,
   g) developing the top and bottom layers with an aqueous alkaline solution.

19. The process according to claim 18 where the antireflective coating is substantially insoluble in a solvent of the top photoresist.

20. The process according to claim 18 where the antireflective layer has a thickness less than the thickness of the photoresist.

21. The process according to claim 18 where the antireflective coating is insoluble in the aqueous alkaline solution prior to the exposing step and becomes soluble prior to the developing step.

22. The process according to claim 18 where the aqueous alkaline solution comprises tetramethylammonium hydroxide.

23. The process according to claim 22 where the aqueous alkaline solution further comprises a surfactant.

* * * * *